United States Patent [19]
Yamaguchi et al.

[11] Patent Number: 5,213,675
[45] Date of Patent: May 25, 1993

[54] REFERENCE ELECTRODE, ION SENSOR AND METHOD OF MANUFACTURING THE SAME

[75] Inventors: Shuichiro Yamaguchi; Takeshi Shimomura; Naoto Uchida, all of Shizuoka; Teruaki Katsube; Noboru Oyama, both of Tokyo, all of Japan

[73] Assignee: Terumo Kabushiki Kaisha, Tokyo, Japan

[21] Appl. No.: 717,645

[22] Filed: Jun. 19, 1991

Related U.S. Application Data

[62] Division of Ser. No. 426,713, Oct. 26, 1989, Pat. No. 5,066,383.

[30] Foreign Application Priority Data

| Oct. 27, 1988 | [JP] | Japan | 63-271784 |
| Feb. 6, 1989 | [JP] | Japan | 1-28464 |
| Apr. 3, 1989 | [JP] | Japan | 1-84551 |

[51] Int. Cl.$^5$ ............................................. G01N 27/26
[52] U.S. Cl. ..................................... 204/418; 204/416; 204/435
[58] Field of Search ............... 204/435, 191.2, 192.11, 204/192.15, 418, 416

[56] References Cited

U.S. PATENT DOCUMENTS

| 3,856,649 | 12/1974 | Genshaw et al. | 204/418 |
| 3,926,764 | 12/1975 | Ruzicka et al. | 204/418 |
| 3,932,233 | 1/1976 | Ruzicka et al. | 204/418 |
| 3,957,612 | 5/1976 | Niedrach et al. | 204/414 |
| 3,957,613 | 5/1976 | Macur | 204/412 |
| 4,053,381 | 10/1977 | Hamblen et al. | 204/416 |
| 4,214,968 | 7/1980 | Battaglia et al. | 204/418 |
| 4,269,682 | 5/1981 | Yano et al. | 204/435 |
| 4,280,889 | 7/1981 | Szonntagh | 204/418 |
| 4,507,194 | 3/1985 | Shimomura et al. | 204/435 |
| 4,610,771 | 9/1986 | Gillery | 204/192.1 |
| 4,753,719 | 6/1988 | Yamaguchi et al. | 204/418 |
| 4,798,664 | 1/1989 | Yamaguchi et al. | 204/418 |
| 4,816,118 | 3/1989 | Oyama et al. | 204/416 |
| 4,839,020 | 6/1989 | Yamaguchi et al. | 204/431 |
| 4,861,454 | 8/1989 | Ushizawa et al. | 204/415 |
| 4,871,442 | 10/1989 | Scardera et al. | 156/662 |
| 4,927,516 | 5/1990 | Yamaguchi et al. | 204/403 |

FOREIGN PATENT DOCUMENTS

| 186286 | 2/1986 | European Pat. Off. |
| 2190399 | 11/1987 | United Kingdom. |
| WO89/04959 | 6/1989 | World Int. Prop. O. |

OTHER PUBLICATIONS

Patent Abstracts of Japan, vol. 11, No. 276, Sep. 1987.
Patent Abstracts of Japan, vol. 12, No. 388, Oct. 1988.

Primary Examiner—John Niebling
Assistant Examiner—Bruce F. Bell
Attorney, Agent, or Firm—Burns, Doane, Swecker & Mathis

[57] ABSTRACT

A reference electrode for generating a reference potential on an ion sensor is disclosed. The reference electrode has a lamination film covering a surface of an electrically conductive substrate and formed by alternately laminating silver halide thin films and hydrophobic resin thin films.

5 Claims, 12 Drawing Sheets

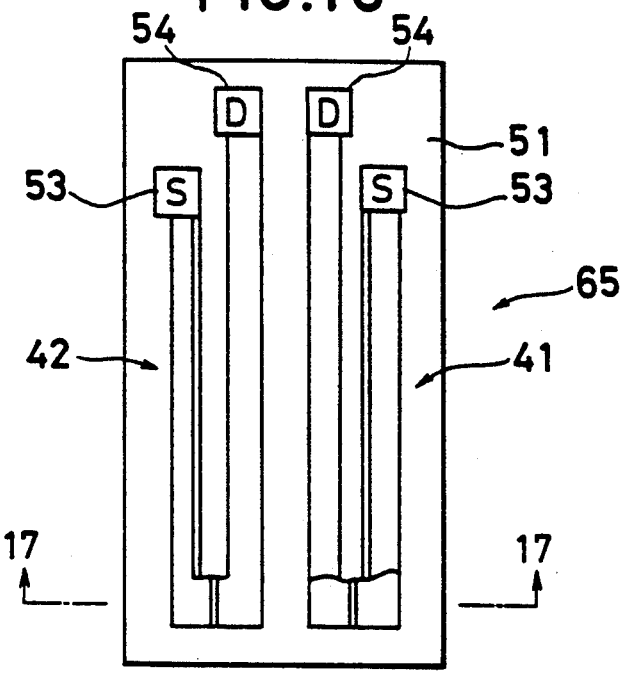
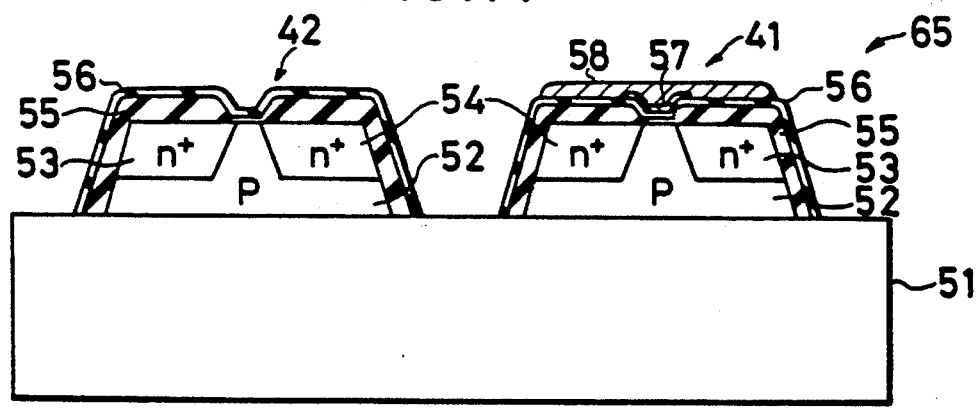
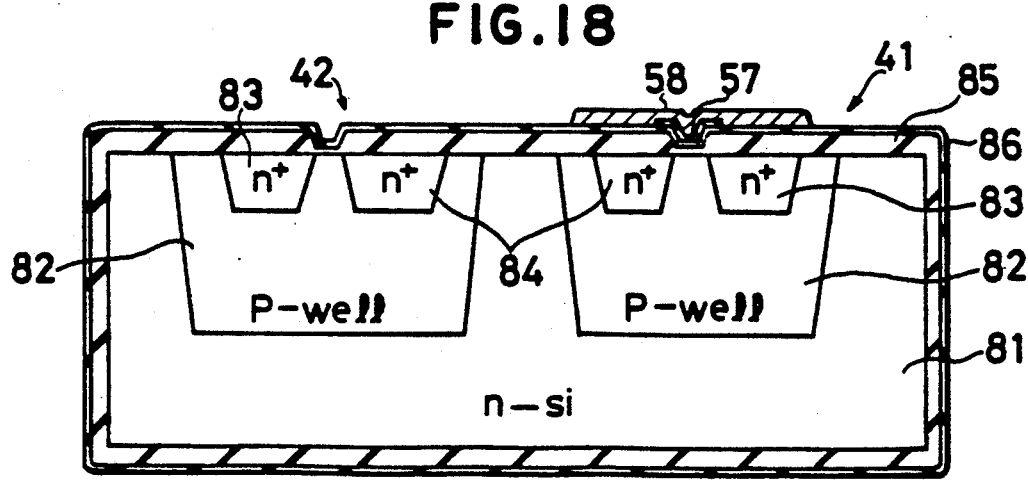

REFERENCE ELECTRODE, ION SENSOR AND METHOD OF MANUFACTURING THE SAME

This application is a divisional of application Ser. No. 07/426,713, filed Oct. 26, 1989, now U.S. Pat. No. 5,066,383.

BACKGROUND OF THE INVENTION

This invention relates to reference electrodes and ion sensors of solid type, which have a polymer film covering a surface of an electrically conductive substrate, and also methods of their manufacture.

Heretofore, as electrochemical reference electrode is selected one, the output potential which is not substantially changed electrochemically while it is in a liquid under test, which is subject to changes in the ion concentration, particularly hydrogen ion concentration. Wellknown examples of such reference electrode are typically saturated calomel electrodes, silver/silver chloride electrodes and hydrogen electrodes. Further, recently researches and investigations are being conducted on commonly termed solid type electrodes, having a film of an organic substance such as polystyrene and parylene, on a gate insulation film of a MOS (metal oxide semiconductor) field-effect transistor (hereinafter referred to as MOS FET).

However, the prior art reference electrodes such as saturated calomel electrodes can be miniaturized with difficulty because there is a liquid junction between reference electrolytic solution and a vessel therefor.

As a method of forming an organic film of polystyrene or the like for a reference electrode, there is a plasma polymerization method (as disclosed in Japanese Patent Disclosures 58-103658 and 58-34352).

Meanwhile, as well-known ion sensors there are one, in which a carbon layer is formed on an insulating layer (for instance of $Si_3N_4$, $Al_2O_3$ or $Ta_2O_5$), one, in which a redox function film (for instance a polymer layer of 1-pyrenamine, 2, 6-dimethylphenol or 4, 4'-biphenol) is formed by an electrolytic polymerization process on an electrically conductive carbonaceous material, and one, in which an ion-sensitive film is formed to cover the redox function film noted above. In order for miniaturization of even these ion sensors, it is proposed to form a structure consisting of a carbon layer, an oxidizing /reducing function film and an ion-sensitive film on a MOS FET gate insulation film or to cover an extended gate electrode surface (as disclosed in Japanese Patent Disclosures 63-131056 and 62-276452).

However, with reference electrodes formed on MOS FET by the plasma polymerization process noted above, the stability of output potential is insufficient because of passage of ion active substances through the polystyrene film mainly due to swelling of the film and also of influence of active residue or functional radicals produced during the electrolytic polymerization.

Further, in an ion sensor formed on MOS FET, the carbon layer formed on the insulating layer is weak in adhesion and mechanical strength and also greatly differs in the expansion coefficients and lattice constants from the redox function film. Therefore, the redox function films is liable to be separated together with the carbon layer from the insulating layer during or after the electrolytic reaction. If the carbon layer is made very thin, for instance below 1,000 angstroms in thickness, although the adhesion is increased, the electric resistance is extremely increased (to 100 $k\Omega/\square$ or above). In such a case, electrolytic reaction can be caused with difficultly. Further, where a coating process or dipping process is used, a chemically obtained polymer can not provide a sufficient function, and a stable potential can not be obtained. For this reason, it is necessary to use a redox function film which is prepared by the electrolytic polymerization process. This film however, is difficultly to solubilize and can not find an adequate solvent.

SUMMARY OF THE INVENTION

This invention has been intended in view of the above problems, and its object is to provide a reference voltage, which can be readily miniaturized, can provide a stable potential without being substantially influenced by the ion concentration and is excellent in stability and durability, and a method of manufacturing the same.

Another object of the invention is to provide an ion sensor, which is capable of miniaturization, is free from the possibility of separation of a redox function film from a base and has a stable function, and a method of manufacturing the same.

To attain the above objects of the invention, there is provided a reference electrode, which comprises an electrically conductive substance, a first lamination film provided on a surface of the substrate and formed by alternately laminating silver halide layers and hydrophobic resin layers and a second lamination film provided on a surface of the first lamination film and formed by alternately laminating hydrophobic resin layers and salt layers.

The second lamination film, like the first one, may be formed by alternately laminating silver halide layers and hydrophobic resin layers as well. In this case, the entire lamination films are constituted by an alternate lamination of silver halide layers and hydrophobic resin layers.

Further, at least one silver halide layer in the second lamination film may contain a salt other than the silver halide, and/or at least one silver halide layer in the second lamination film may be replaced with a layer of a salt other than the silver halide.

Suitable examples of the salt other than the silver halide are potassium chloride, sodium chloride, ammonium chloride, lithium chloride and other halide salts. Further, the salt may be other than halide salts, e.g., sodium nitrate and sodium sulfate.

Further, a mixture film of a mixture consisting of a silver halide, a halide salt and hydrophobic resin may be formed on a surface of the second lamination film According to the invention, there is further provided a reference electrode, which comprises an electrically conductive substrate, a lamination film provided on a surface and formed by alternately laminating silver halide layers and hydrophobic resin layers and a mixture film formed on the lamination film and of a mixture consisting of a silver halide, a halide salt and a hydrophobic resin or a lamination film formed on a surface of the electrically conductive substrate and formed by laminating halide salt layers containing an oxidizing agent and hydrophobic resin layers.

The halide salt layers may contain a silver halide.

The electrically conductive substrate is made of silver or consists of a silver layer formed on an insulator surface, and the silver halide is suitably a member of a group consisting of silver chloride, silver bromide, silver iodide and silver fluoride. The hydrophobic resin may be any resin having hydrophobicity, e.g., polyolefin, polystyrene, polyimide, polycarbonate, polymethylmethacrylate (PMMA), polytetrafluoroethylene, polyvinyl fluoride, polyvinylidene fluoride and other fluorine resins. Polytetrafluoroethylene is particularly suitably used.

A hydrophilic film, a gel film, or an ion-permeable film may suitably be formed on a surface of the lamination film or mixture film for improving the antithrombic separation of trapped matter and ions or passage of ions, particularly chlorine ions. These films may suitably be perfluoro ion-exchange films of polyvinyl chloride-polyethyleneglycol copolymer, styrene-hydroxyethylmethacrylate (HEMA), styrenehydroxyethyl-methacrylate block polymer, polyurethane, polyvinyl alcohol, polyhydroxymethyl-methacrylate, polyacrylamide gel, nafion (trademark), etc.

The halide salt layers and the like are formed by a vacuum deposition process, a sputtering process, an ion plating process, a cluster ion beam process, etc., while the hydrophobic resin layers are formed by a CVD (chemical vapor deposition) process, and ion plating process, a cluster ion beam process, a plasma polymerization process, a sputtering process, a photoresist process, etc.

With the reference electrode according to the invention, the lamination film may be formed on a surface of a gate insulation film of a field-effect transistor either directly or via a thin layer of silver.

When the reference electrode having the above construction according to the invention is immersed in an aqueous solution, water molecules pass through thin layer of hydrophobic resin in the lamination film to reach a silver halide layer or halide layer, and a fixed concentration of halide ions are provided in each halide layer. Thus, a constant potential is generated in the first silver/silver halide layer. In other words, each halide layer has a role of the reference electrolyte and reference electrolyte chamber in the conventional reference electrode. Thus, this reference electrode permits determination of ion concentration by immersing it together with an ion electrode in an aqueous solution to use it as electrode for reference potential generation in the ion concentration measurement and measuring the potential difference between the reference electrode and ion electrode.

Particularly, where the second lamination film contains a halide salt such as potassium chloride or sodium chloride as a thin film or as a component of a mixture, dissociated chlorine ions are supplied through the hydrophobic resin layer to the neighborhood of silver halide layer. Therefore, silver ions and chloride ion can be held sufficiently inside the electrode. It is thus possible to effectively prevent silver ions from flowing out to the outside by preventing liquidation of silver chloride which takes place with the lapse of time. This permits prevention of the deterioration of the characteristics of the reference electrode to obtain stabilization and life extension.

In case of a solution under test, which is free from halogen ions, contamination of the solution by a halogen-halide is liable. In such a case, it is possible to use a salt other than halides.

The reference electrode according to the invention is solid as noted before, and can be readily miniaturized. Further, it is with difficulty influenced by the pH and chlorine ion concentration and can provide a constant potential, thus improving the stability and durability. Further, the lamination film can be formed under the room temperature condition for an atom beam sputtering apparatus can be used. Thus, high dimensional accuracy of pattern formation can be obtained, and mass production is possible by performing the formation in a semiconductor manufacture process. Further, since the intended function can be obtained with 1,000 angstroms or below of the thickness of the lamination film, the reference electrode may be utilized in a form integrated with a sensor in an ultramicro area of the order of microns.

According to the invention, there is further provided a reference electrode, which comprises an electrically conductive substrate and a lamination film formed on the substrate and including a silver halide layer formed by a neutral beam sputtering process or a deposition process and hydrophobic resin layer formed by a neutral beam sputtering process on the silver halide layer. According to the invention, there is further provided a reference electrode, which comprises a gate insulation film of a field-effect transistor and lamination film including a silver halide layer formed by a neutral beam sputtering process on a surface of the gate insulation film and a hydrophobic resin layer formed by a neutral beam sputtering process on the silver halide layer. It is possible to form the lamination film on a thin layer of silver formed in advance on the gate insulation film surface of the field-effect transistor. The electrically insulating substrate may be a silver layer or obtained by forming a silver layer on an insulator surface.

The silver halide is suitably a member of a group consisting of silver chloride, a silver bromide, silver iodide and silver fluoride. For the hydrophobic resin layer may be used fluorine resins and polytetrafluoroethylene (available under a trademark "Teflon"), and its thickness is 2.0 angstroms to 10 microns, preferably 10 to 1,000 angstroms.

According to the invention, there is further provided a method of manufacturing a reference electrode, which comprises a step of forming targets of a silver halide and a hydrophobic resin by an electrolytic polymerization process on a predetermined substrate surface and a step of sputtering the silver halide and hydrophobic resin targets by alternate bombardment thereof with a neutral beam to thereby form a lamination film consisting of silver halide layers and hydrophobic layers on the substrate surface.

According to the invention, there is further provided an ion sensor, which comprises an electrically conductive substrate, an oxidizing/reducing function film formed there by a neutral beam sputtering process on a surface of the substrate and an ion-sensitive film covering the redox function film. According to the invention, there is further provided an ion sensor, which comprises a gate insulation film of a field-effect transistor, and redox function film formed by a neutral beam sputtering process on the gate insulation film surface and and ion-sensitive film covering the redox function film.

For the redox function film may be used poly-(4,4'-biphenol), poly-(2, 6-dimethylphenol), poly-(1,2-diaminobenzene), poly-(1-pyrenamine) and polyaniline.

The ion-sensitive film may be of fluorosilicate glass, or it may be a liquid film such as a hydrogen ion carrier film, a Na ion carrier film and K+ ion carrier film. The ion carrier may be tri-n-dodecylamine, bis-(12-Crown-4), etc.

According to the invention, there is further provided a method of manufacturing an ion sensor, which comprises a step of forming a target of a redox function substance by an electrolytic polymerization process on a predetermined substrate surface, a step of sputtering the redox function substance target by bombardment thereof with a neutral beam to thereby form a redox function film on a sensor substrate surface an a step of forming and ion-sensitive film on a surface of the redox function film.

As shown, since the reference electrode according to the invention is a solid electrode with a lamination film formed on an electrically conductive substrate or a gate insulation film of a field-effect transistor and consisting of silver halide layers and hydrophobic resin layers, the inner liquid chamber and liquid junction that are necessary with the conventional electrode are unnecessary, so that it is possible to realize miniaturization. When this reference electrode is immersed in an aqueous solution, the hydrophobic resin layer swells. Since it is very thin (not thicker than 10 microns), water can migrate into the lamination film to cause dissociation of the silver halide. In other words, the lamination film itself can serve the role of an inner liquid. Further, the hydrophobic layer can pass ions only very slightly and also has a laminar structure, and thus it can prevent flow-out of ions in it. This hydrophobic resin layer serves the role of the liquid junction. Thus, the reference electrode according to the invention can provide a stable potential like the conventional reference electrode having an inner liquid chamber. Further, of the lamination film the silver halide layers are formed by the neutral beam sputtering process or a vapor deposition process, while the hydrophobic resin layers are formed by the neutral beam sputtering process. Thus, the electrode can be miniaturized and also can be formed together with other ion sensors on a common chip, thus facilitating the manufacture of integrated sensors.

Further, with the ion sensor according to the invention the redox function film is formed on an electrically conductive substrate or on a gate insulation film of a field-effect transistor by the neutral beam sputtering process, i.e., by forming a controlled film of a redox function substance by the electrolytic polymerization process on a predetermined electrode surface and using this redox function substance as target for bombardment. Thus, it is possible to form a redox function film that has the same composition as the preliminarily formed electrolytic polymer film on the surface of an electrically conductive substrate or the like. Therefore, unlike the prior art, there is no need of connecting lead to electrode for electrolytic reaction or insulating unnecessary portions. It is thus possible to readily form a controlled film, and there is no possibility of separation of the redox function film. Further, the use of the preliminarily electrolytically polymerized redox function film as target permits use of a film having known characteristics. In other words, it is possible to manufacture an ion sensor having a definite characteristic and a stable function. Further, since a neutral atom beam is used, there is no possibility of destruction by charging and discharging. It is thus possible to form a film on even a mechanically weak portion such as a gate section of a MOS field-effect transistor and readily obtain miniaturization.

For the ion sensor according to the invention, it is possible to use a junction type or Schottky gate type field-effect transistor as well as the MOS field-effect transistor.

BRIEF DESCRIPTION OF THE DRAWINGS

FIG. 16 is a plan view showing an integrated ISFET sensor as Embodiment 15 of the invention;

FIG. 17 is a sectional view taken along line 17—17 in FIG. 16;

FIG. 18 is a plan view showing an ISFET sensor as Embodiment 16 of the invention;

DESCRIPTION OF THE PREFERRED EMBODIMENTS

Now, preferred embodiments of the invention will be described in detail with reference to the drawings.

(Embodiment 1)

Figure 1:
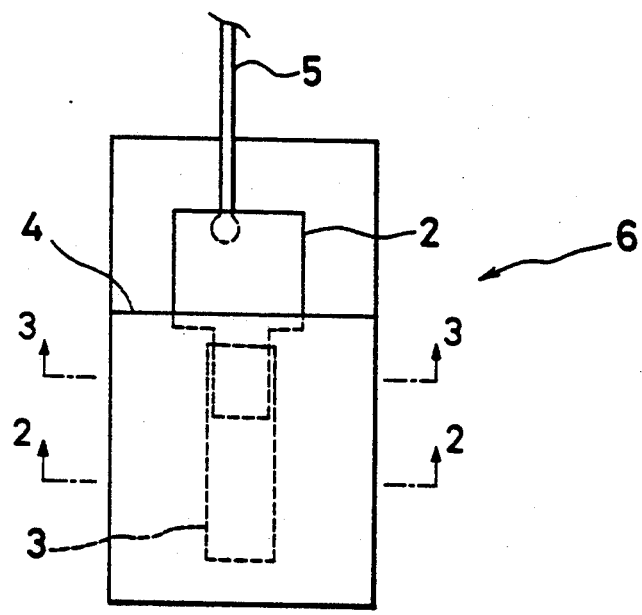
FIG. 1 is a plan view showing a reference electrode as Embodiment 1 of the invention.
Figure 2:
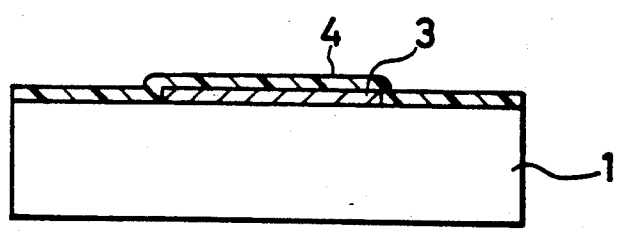
FIG. 2 is a sectional view taken along line 2—2 in FIG. 1.
Figure 3:
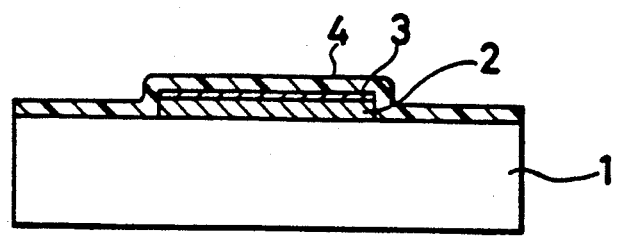
FIG. 3 is a sectional view taken along line 3—3 in FIG. 1.
Figure 4:
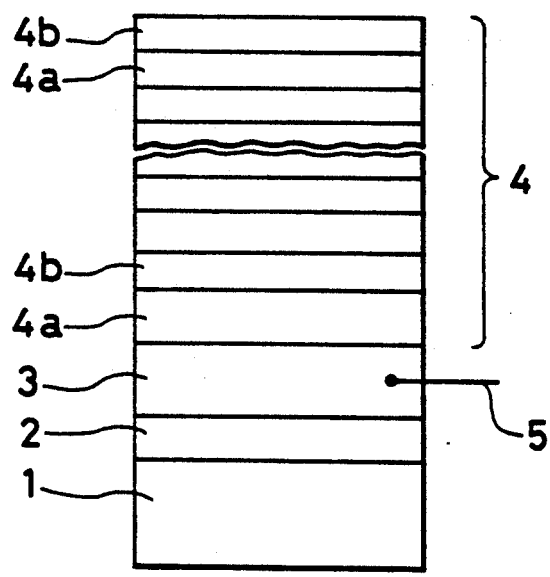
FIG. 4 is a schematic view illustrating the sectional structure of the same reference electrode.

An electrode base was prepared by forming, on the back surface of a sapphire substrate 1 (having a face orientation of ($1\bar{1}02$) and a size of 15 mm by 15 mm by 0.4 mm) as shown in FIG. 1, a pattern of a thin layer 2 of chromium with a thickness of about 500 angstroms and then a pattern of a thin layer 3 of silver with a thickness of about 1,000 angstroms by a lift-off process using a DC sputtering apparatus (manufactured by Arnerba Inc.). The same electrode pattern as shown in FIG. 1 was also formed on a surface of an isotropic alumina substrate and on a surface of a glazed alumina substrate. Then, a target of silver chloride and a target of a polytetrafluoroethylene resin (available under a trademark "Teflon") were alternately bombarded each 0 for every 30 minutes with a high-speed argon atom beam (1.15 to 1.2 mA in current level), provided by an atom beam sputtering apparatus by ionizing argon gas at 7 kV, then accelerating it and then neutralizing it again by providing an electron shower for causing particles flying out from the targets to be deposited on the surface of the electrode base, thus forming a lamination film 4 with a thickness of 300 to 500 angstroms as shown in schematic sectional profile in FIG. 4. The silver chloride layers 4a and polytetrafluoroethylene resin layers 4b in the lamination film 4 each had a thickness of 30 to 50 angstroms Then, a lead 5 was connected to the chromium thin layer 2 of the electrode base using an electrically conductive adhesive (available under a trade name "C-850-6" by Amicon Co., Ltd.). Thereafter, a silicone resin (PR 305, clear, Tore Silicone Co., Ltd.) was coated as insulator to conceal the connected portion of the lead 5 as well as chromium and silver thin layers 2 and 3 and then dried, thus completing the reference electrode 6.

Experiment Example 1

Figure 5:
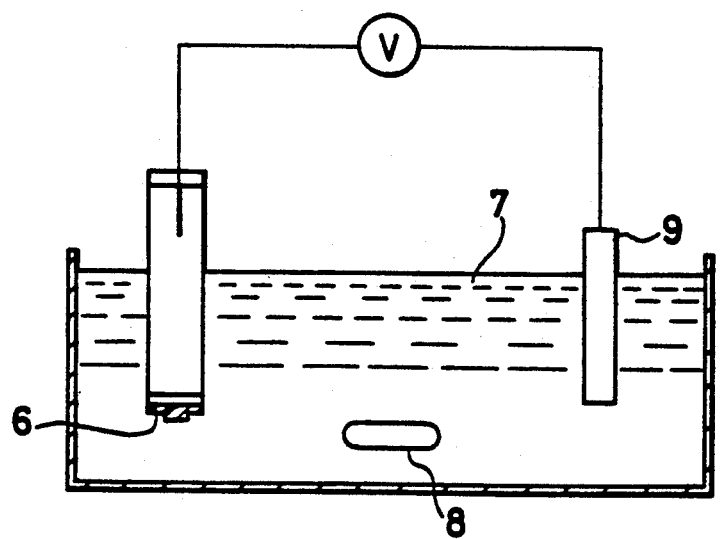
FIGS. 5 and 6 are schematic views showing apparatuses for measuring the characteristics of the reference electrode.
Figure 7:
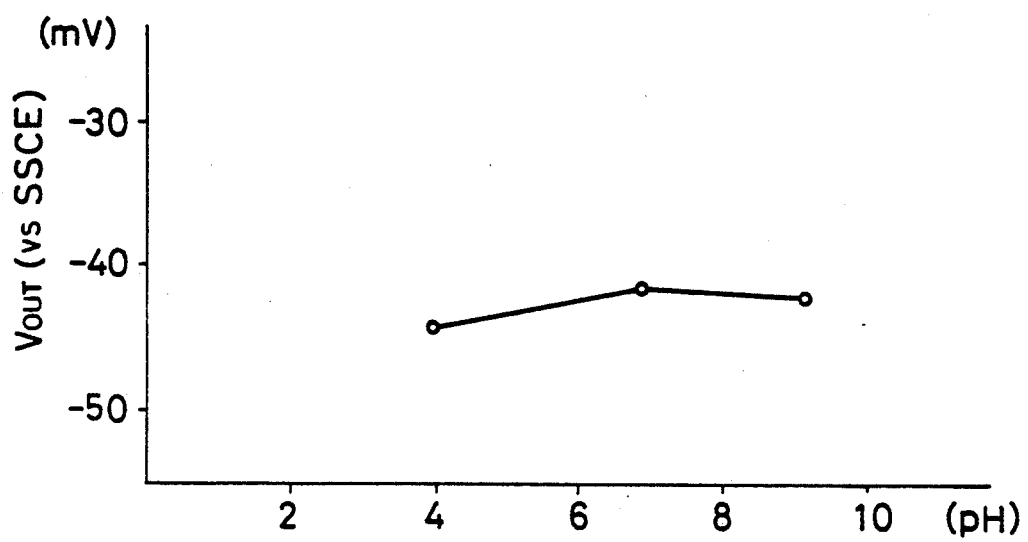
FIG. 7 is a graph showing the pH dependency of the reference electrode potential in Embodiment 1.

The reference electrode 6 thus produced was held immersed in a 50-mM phosphate buffer liquid (with pH of 7.4) for 0,25, 45, 161 and 288 hours. Then, it was immersed together with a commercially available saturated sodium chloride calomel electrode (hereinafter referred to as SSCE) 9 in a phosphate buffer liquid (with pH of 7.4, 50 mM) containing 0.154 M of sodium chloride, as shown in FIG. 5, and the output potential (Vout) of the electrode 6 with respect to the SSEC 9 was measured while agitating the buffer liquid with an agitator 8. FIG. 7 shows the output potential of the electrode corresponding to the pH of the solution. It will be seen that the reference electrode in this embodiment provides a substantially constant potential irrespective of the pH. However, the electrodes using substrates other than the sapphire substrate for the electrode base had weak durability, and their life was about 40 days.

Experiment Example 2

Figure 8:
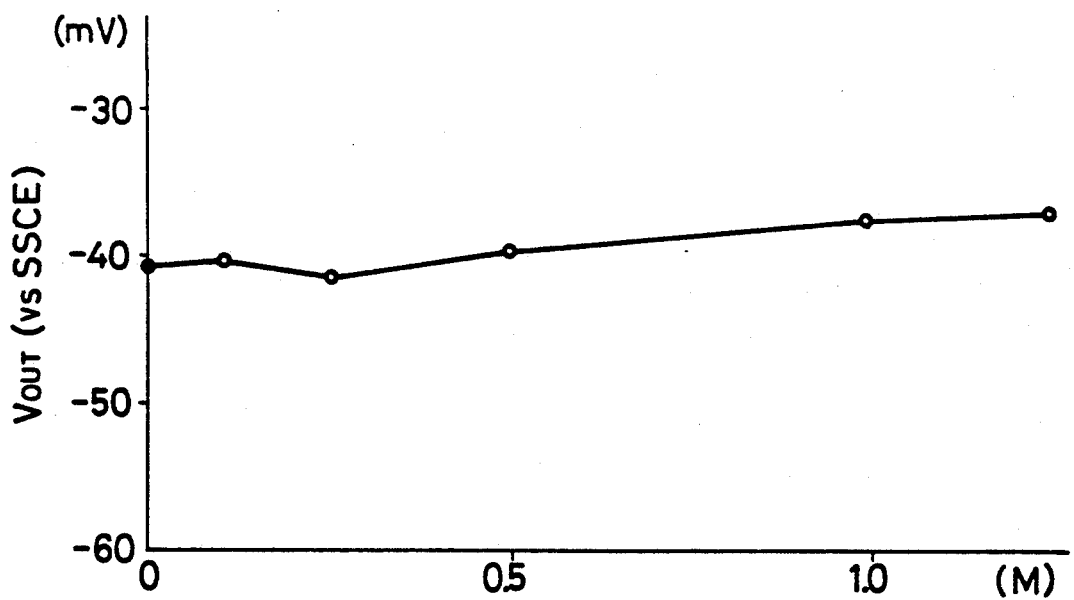
FIG. 8 is a graph showing the chlorine ion concentration dependency of the same reference electrode potential.

The reference electrode 6 produced in Embodiment 1 by using the sapphire substrate was held immersed in a saturated sodium chloride aqueous solution for 45 days after the production, and during this time the chloride ion concentration dependency of the potential was evaluated. The same measurement method as in Experiment example 1 was adopted except for using a standard buffer solution with pH of 6.86 as liquid under test, varying the chloride ion concentration of the solution by dissolving sodium chloride in the solution and measuring the output potential with respect to the SSEC 9 at this time. FIG. 8 shows the output potential of the electrode corresponding to the chlorine ion concentration in the solution. As is seen, the reference electrode 6 in this embodiment provides a substantially constant potential irrespective of the chlorine ion concentration. Characteristics of the electrode were also examined after preserving the electrode in the solution noted above for 100 days. It was found that the electrode is not influenced by the pH so long as the pH is in a range of 4 to 9.2, and also no potential change was recognized in a chlorine ion concentration range of 0 to 1 M.

(Embodiment 2)

Figure 9:
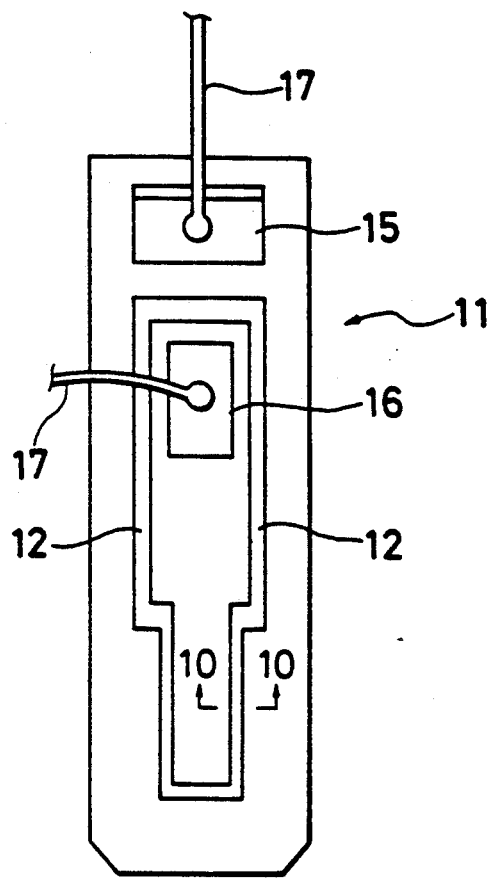
FIG. 9 is a plan view showing the structure of a reference electrode as Embodiment 2 of the invention.
Figure 10:
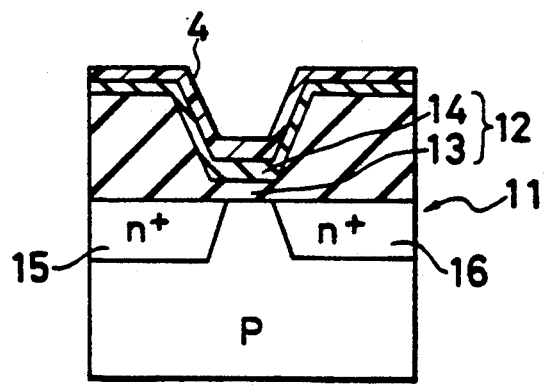
FIG. 10 is a sectional view taken along line 10—10 in FIG. 9.

As shown in FIGS. 9 and 10, on a surface of a gate insulation film 12 of a MOS ISFET (ion-selective field-effect transistor) 11 was formed a lamination film 4 including a silver chloride layer and a polytetrafluoroethylene resin layer by the same method as in Experiment example 1. The lamination film 4 had a thickness of about 700 angstroms, and it was formed by laminating 10 layers. For the gate insulation film 12 a pH-ISFET electrode having an insulation film structure of a 1,000-angstrom silicon oxide film 13/ a 1,500-angstrom nitride film 14 was used, and leads 17 were connected in advance to source and drain regions 15 and 16. FIG. 10 shows a sectional structure taken along line 10—10 in FIG. 9.

Experiment Example 3

Figure 6:
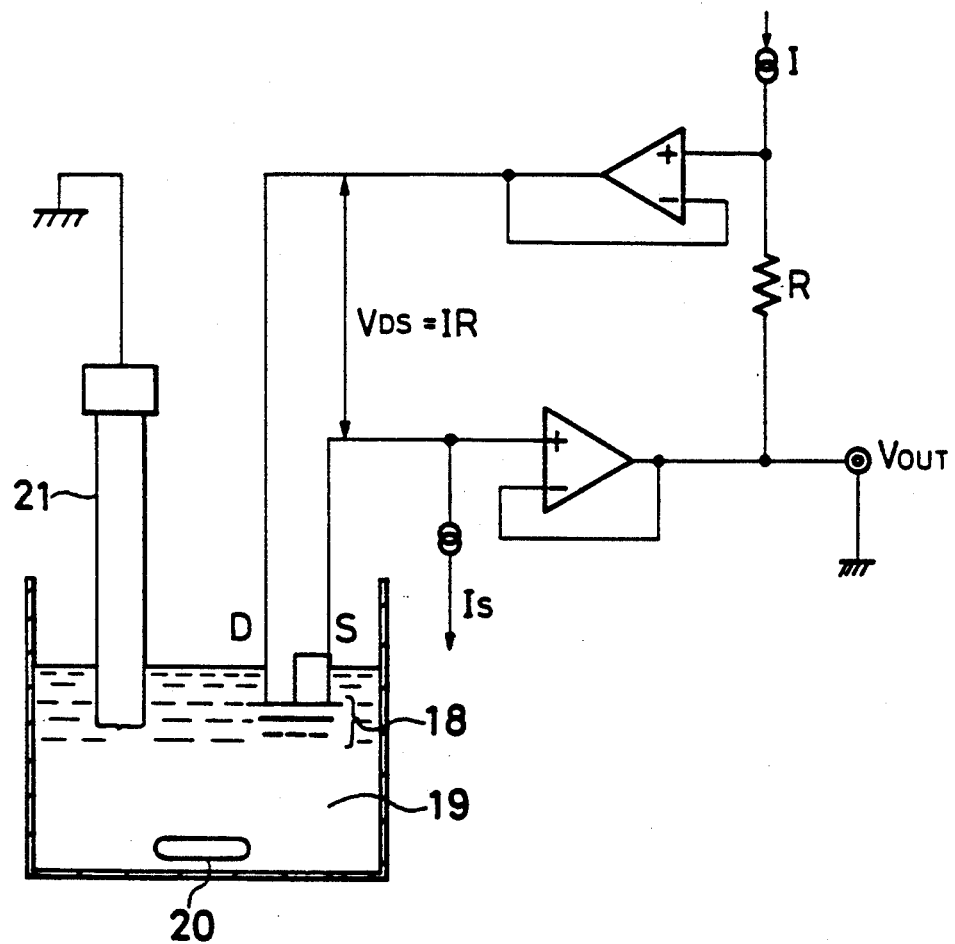

The reference electrode 18 in Embodiment 2 was held immersed in a phosphate buffer solution 19 in the measuring apparatus shown in FIG. 6, and the output potential (Vout) of the electrode 18 with respect to the SSEC 21 was measured while agitating the phosphate buffer solution 19 with an agitator 20 for examining the pH dependency and chlorine ion concentration dependency of the output potential. The electrode provided a constant potential within experimental errors ($\pm 1$ mV) in a pH range of 1 to 10, showing substantial freedom of the electrode from the dependency on pH and chlorine ion concentration. The measurement was performed with $V_{ps}=4$ V and $I_s=50$ $\mu$A. It was found that the gate potential was shifted in the negative direction by 1.0 to 1.5 V with respect to a pH electrode free from the lamination film 4. However, the electrode can be utilized sufficiently as a reference electrode for a semiconductor sensor so long as a shift of the output voltage is made.

(Embodiment 3)

Figure 11:
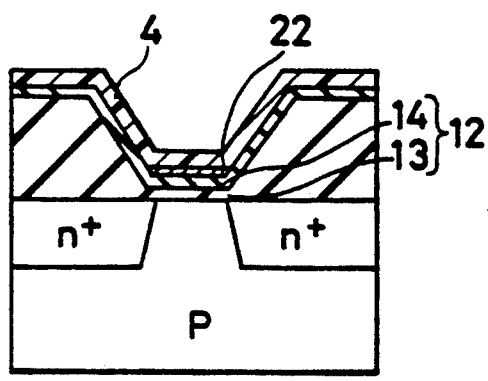
FIG. 11 is a sectional view showing a reference electrode as Embodiment 3 of the invention.

A thin film 22 of silver (with a thickness of 50 to 300 angstroms) was formed by vacuum deposition on a surface of a gate insulation film 12 of a ISFET, as shown in FIG. 11, in the same manner as in Embodiment 2. Then a lamination film 4 (with a thickness of 700 angstroms) consisting of a silver chloride layer and a polytetrafluoroethylene layer was formed on the entire surface the silver chloride film 22 in the same manner as in Embodiment 1.

Experiment Example 4

Of this reference electrode, the dependency on pH and chlorine ion concentration was examined in the manner as in Experiment example 3. It was found that the electrode was free from the dependency in a pH range of 1 to 10 and in a chlorine ion concentration range of 0 to 1M. Further, great negative shift of the gate potential as in Embodiment 2 was not observed.

(Embodiment 4)

Figure 12:
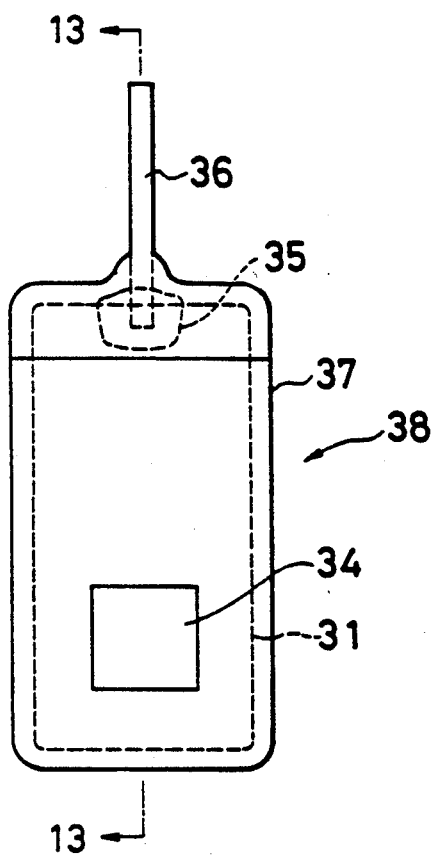
FIG. 12 is a plan view showing the structure of a reference electrode as Embodiment 4 of the invention.
Figure 13:
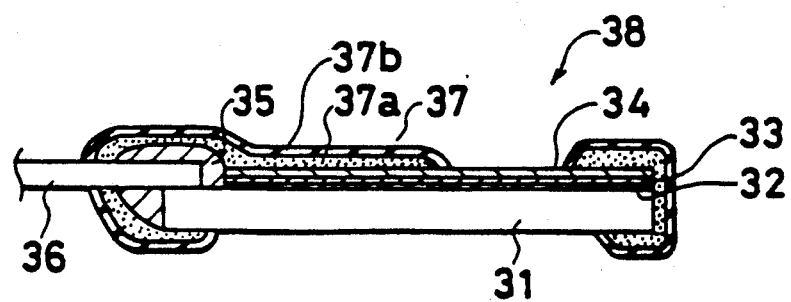
FIG. 13 is a sectional view taken along line 13—13 in FIG. 12.
Figure 14:
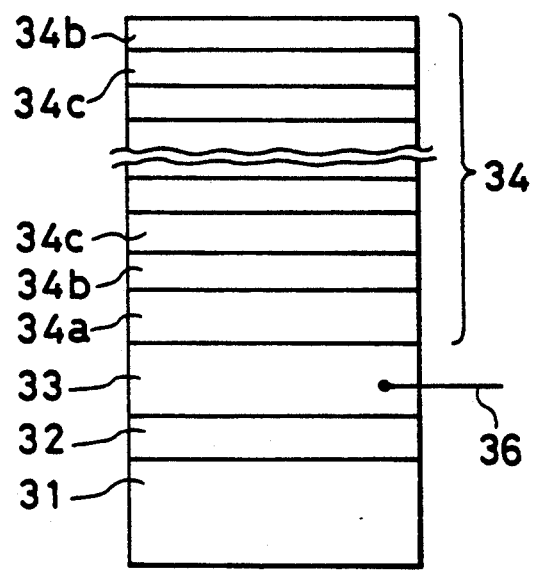
FIG. 14 is a schematic view showing the sectional structure of a reference electrode as embodiment 4.

As shown in FIGS. 12 and 13, an electrode base was prepared by forming, on the back surface of a sapphire substrate 31 (having a face orientation of (1$\bar{1}$02) and a size of 15 mm by 15 mm by 0.4 mm), a pattern of a thin layer 32 of chromium with a thickness of about 500 angstroms and then a pattern of a thin layer 33 of siler with a thickness of about 1,000 angstroms by a lift-off process using a DC sputtering apparatus. The same electrode pattern as shown in FIG. 12 was also formed on a surface of an isotropic alumina substrate and also on a surface of a glazed alumina substrate. Then, targets of silver chloride, polytetrafluoroethylene resin and potassium chloride were alternately bombarded with a high-speed argon atom beam (1.2 mA in current level, incidence angle of 30 to 45 degrees), provided by an atom beam sputtering apparatus by ionizing argon gas at 7 kV, then accelerating it and then neutralizing it again by providing an electron shower for causing particles flying out from the targets to be deposited on the surface of the electrode base, thus forming a lamination film 34 with a thickness of about 2,500 angstroms. The silver chloride layers 34a, polytetrafluoroethylene resin layers 34b and potassium chloride layers 34c of the lamination film 34 each had a thickness of about 50 angstroms. Then, a lead 36 is connected to the silver thin layer 33 of the electrode base using an electrically conductive adhesive 35 (c-850-6, Amicon Inc.). Thereafter, an insulating film 37 consisting of an epoxy resin layer 37a and a Teflon coat enamel film 37b was provided to conceal the connected portion of the lead 36 and chromium and silver thin layers 32 and 33, thus completing the reference electrode 38 (FIG. 12).

Experiment Example 5

Figure 15:
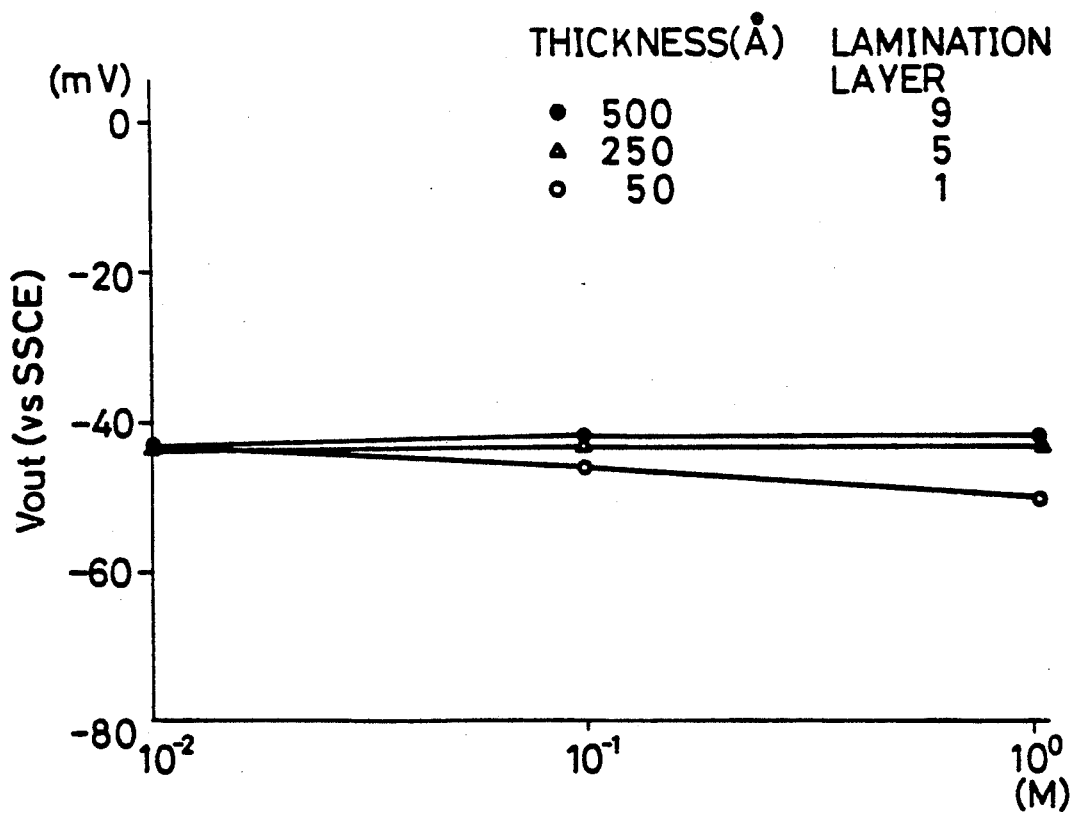
FIG. 15 is a graph showing the chlorine ion dependency in Experiment examples 5 and 6.

The reference electrode 38 thus produced was held immersed together with SSEC in phosphate buffer solutions with chlorine ion concentrations of 0.001, 0.1 and 1.0 M, and the output potential (Vout) of the electrode 38 with respect to the SSCE was measured while agitating the solution with an agitator. FIG. 15 shows the output potential of the electrode corresponding to the chlorine ion concentration of the solution.

It is thus confirmed that the reference electrode of this embodiment provides a substantially constant potential irrespective of the chlorine ion concentration.

Further, the characteristics of the electrode were examined after preserving the electrode in the solution noted above for 100 days. It was found that the output potential is free from the influence of the pH in a range of 4 to 9.2 and also is free from influence by chlorine ion concentration in a range of 0 to 1 M.

(Embodiment 5)

A lamination film with a thickness of 500 angstroms was formed by alternately laminating silver chloride layers, polytetrafluoroethylene layers and potassium chloride layers by the method as in Embodiment 4, and then lead is connected to complete a reference electrode.

(Embodiment 6)

A lamination film with a thickness of 50 angstroms by alternately laminating silver chloride layers, polytetrafluoroethylene layers and potassium chloride layers in the manner as in Embodiment 5.

Experiment examples 6 and 7

The output potentials of the reference electrodes in the embodiments 5 and 6 with respect to the SSCE were measured in the manner as in Experiment example 5. FIG. 15 shows the result. The reference electrode in Embodiment 5 provided a substantially constant potential irrespective of chlorine ion concentration. The reference electrode in Embodiment 6, Which had a small film thickness, could not prevent flowout of chlorine ions, and therefore showed a slight slope of the plot of the output potential versus chlorine ion concentration.

(Embodiments 7 to 9)

A thin film of chromium with a thickness of about 100 angstroms was formed on a surface of a sapphire substrate (having a face orientation on a (1002) using a DC sputtering apparatus. Then, a silver chloride layer with a thickness of 300 angstroms and containing 0.1 to 10% of sodium chloride and then a thin layer of silver with a thickness of about 500 angstroms were formed on a surface of the silver thin layer using a vacuum deposition apparatus.

Then, a polytetrafluoroethylene thin film with a thickness of about 100 angstroms was formed to cover the silver chloride layer by causing bombardment of a polytetrafluoroethylene target by a neutral argon beam using a neutral atom sputtering apparatus (Embodiment 7).

Then, the silver chloride thin layer and polytetrafluoroethylene thin layer were formed repeatedly four times and eight times, respectively (Embodiments 8 and 9).

An end portion of lead was masked as connected portion with an aluminum bottle lest the polytetrafluoroethylene and silver chloride thin layers should be formed on it. Subsequently, a thin covered copper wire was bonded using a silver paste, and then insulation was provided with an epoxy resin adhesive except for a central area of about 2 mm by 2 mm. Then, for further insulation a Teflon coat enamel film (Daikin Kogyo Co, Ltd.) was formed under process conditions of 100° to 110° C. and 45 minutes.

Experimental Example 8

The electrodes produced in Embodiments 7 to 9 were each held immersed as function electrode together with a SSCE in a sample solution, and their electromotive force response was measured using an electrometer (manufactured by Advan Test Co., Ltd.). More specifically, the pH dependency was examined using standard buffer solutions with pH of 4.01, 6.86 and 9.18. The reference electrodes of Embodiments 7 to 9 were all free from influence of the pH. Further, the chlorine ion concentration dependency was examined by varying the chlorine ion concentration to 0.01, 0.1 and 1 M by adding sodium chloride while holding a constant pH (of 6.86). The electrodes of Embodiments 7 to 9 all came to show a potential close to a theoretical level ($-40$ mW with respect to SSCE) in about one hour from the instant when they were immersed in solution.

It was thus found that quick initial stabilization could be obtained by incorporating a chloride salt in the silver chloride layer.

(Embodiment 10)

A silver layer with a thickness of 500 angstroms was formed on a sapphire substrate in the manner as shown in FIG. 7, and then a silver chloride layer with a thickness of about 300 angstroms was formed using a vacuum deposition apparatus.

Then, a solution obtained by dissolving 0.5 to 1% of polymethyl-methacrylate (PMMA, with a molecular weight of $10^6$ to $10^7$) in a methylisobutylketone (MIBK) as solvent was coated on the silver chloride layer using a spin coating apparatus and under conditions of 1,000 rpm and 30 seconds. The coating was then dried at 110° C. for 30 minutes and then thermally processed at 170° C. for 10 minutes, thus forming a polymethylmethacrylate film with a thickness of 500 to 1,000 angstroms. Then, a silver chloride layer containing 1% of sodium chloride was formed using a vacuum deposition apparatus to cover the polymethyl-methacrylate film. Then a polymethyl-methacrylate film with a thickness of 500 angstroms was formed in the same method as described above. In the above way, the silver chloride layer containing sodium chloride and polymethyl-methacrylate layer were laminatingly formed alternately ten times. A lead end portion was masked as connected portion with a tape of polyimide (available under a trademark "Capton"), and after formation of the lamination film the tape was peeled off, and the lead (i.e., thin copper wire) was bonded using a silver paste. Then, the entire base was covered for insulation with an epoxy resin adhesive and a Teflon coat enamel film such as to expose a central portion with about 2 mm by 2 mm of the polymethyl-methacrylate film.

(Embodiment 11)

A reference electrode was produced in the same manner as in Embodiment 10 except for that "Fluororesist" (a trademark by Daikin Kogyo Co, Ltd.) was used in lieu of polymethylmethacrylate. "Fluororesist" contains a resin obtained by grafting a fluorine-based polymer in polymethyl-methacrylate.

(Embodiment 12)

A reference electrode was produced in the same manner as in Embodiment 7 except for that a polyimide-based photoresist (for instance "Photoneese", a trademark by Tore Co., Ltd.) in lieu of polymethyl-methacrylate. In this case, however, every time the photoresist was coated, prebaking was subsequently done at 110° C. for 20 minutes, and then UV ultraviolet exposure was done, and postbaking was done several times at 180° to 400° C.

(Embodiments 13 and 14)

A lamination film consisting of a silver chloride layer and a polytetrafluoroethylene resin layer was formed on a surface of a gate insulation film of a MOS ISFET in the manner as in Embodiments 7 to 12. As gate insulation film was used a silicon wafer with an insulating film consisting of a silicon oxide layer (1,000 angstroms thick) and a silicon nitride layer (1,500 angstroms thick). A silver/silver chloride layer and a silver chloride layer were deposition formed on the ISFET substrate surface, and an electrode pattern was formed on and in the neighborhood of the gate insulation film by a lift-off process.

In Embodiment 13, the polytetrafluoroethylene resin layer was formed only on a gate insulation section using a metal mask and a neutral argon atom beam sputtering apparatus, while forming the silver chloride layer using a vacuum deposition apparatus. In Embodiment 14, the polyimide-based photoresist was spin-coated to a thickness of 500 angstroms and then exposed and developed using a photomask to selectively leave a resist film on the gate insulation film only. Subsequently, postbaking was done at about 400° C., and a silver chloride layer was deposited using a metal mask.

Lamination film was formed in this way, and then a photoresist film was formed over the entire surface, followed by UV exposure leaving source and drain electrode contact sections and postbaking at 180° to 400° C. for insulation.

Experiment Example 9

The reference electrodes produced in Embodiments 10 to 12 were tested to examine the pH and chlorine ion concentration dependencies of the output potential using the same method as in Experiment example 8. It was found that there was substantially no influence by pH in a pH range of 2 to 10 and also influence by the chlorine ion concentration was not substantial. Further, after immersion in solution values near the theoretical value (−40 mV, with respect to SSCE) could be obtained in 30 minutes to 5 hours.

Experiment example 10

The FET electrodes produced in Embodiments 13 and 14 were each connected to an ISFET driver, and their output potential with respect to SSCE was measured in the manner as in Experiment example 8. It was found that the output voltage was stable and independent of the pH and chlorine ion concentrations.

Now embodiments of the invention concerning ion sensors will be described. First, the neutral beam sputtering process employed according to the invention will be explained.

In the neutral beam sputtering process, a rare-gas element having a high sputtering factor is introduced into a reaction chamber to be ionized by a cold cathode or the like and then accelerated in a high voltage electric field before being passed through an electron atmosphere for neutralization. High-speed neutral particles (i.e., neutral beam) thus obtained are used to bombard a target. A sputtering phenomenon that takes place at this time is utilized to form a thin film on an intended substrate. Unlike the vacuum deposition process or ion infection process, which utilizes movement of energy, in the sputtering process the kinetic energy of rare gas is directly converted to kinetic energy of atoms or molecules of the target, and by this process a dense thin film can be formed from even a high-melting material or alloy.

The neutral beam suitably does not substantially contain ions (usually containing 1% or below of ions). A neutral beam containing ions is undesired because it is liable to cause charge-up or discharge of decomposition of an insulating material or organic material due to ions.

Particularly, in the neutral atom beam sputtering process, ion particles are not substantially contained. Therefore, pin hole formation or composition change at the time of the thin film formation is less liable, and also satisfactory thin film reproducibility can be obtained.

(Embodiment 15)

FIG. 16 is a plan view showing an ion sensor for a MOS ISFET (ion-sensitive field-effect transistor) using the reference electrode in Embodement 15 of the invention. FIG. 17 is a sectional view taken along line 17—17 in FIG. 16. This ISFET ion sensor comprises a reference electrode section 41 and a sensor section 42. This ISFET ion sensor was manufactured by the following method. First, islands of a p-type silicon layer 52 were formed by etching on areas of a surface of a SOS (silicon sapphire) substrate 51 of 2 mm by 5 mm by 0.5 mm, in which the reference electrode section 41 and sensor section 42 were to be formed. Source and drain regions 53 and 54 were then formed through impurity diffusion after a process of manufacture of an n-channel MOS FET. Then, a film 55 of silicon oxide (SiO) with a thickness of 100 angstroms was formed as insulating film by thermal oxidation on gate sections of the reference electrode and sensor sections 41 and 42, and then a film 56 of silicon nitride ($Si_3N_4$) with a thickness of 200 angstroms was formed by, for instance, a CVD (chemical vapor deposition) process. Further, a silver layer 57 was formed by the vacuum deposition process on the gate section of the reference electrode section 41.

Figure 19:
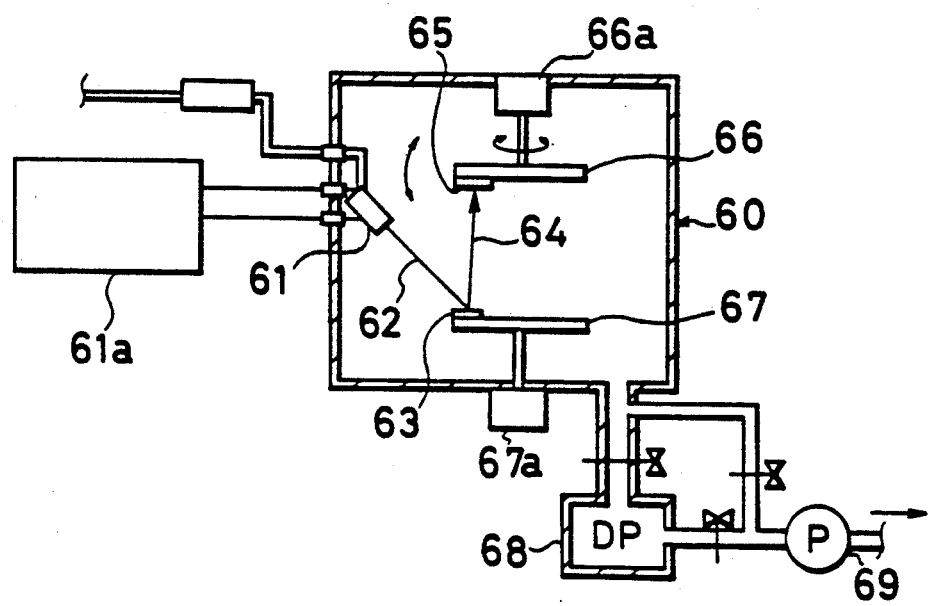
FIG. 19 is a schematic view showing a neutral beam sputtering apparatus.

Subsequently, a lamination film 58 was formed on the reference electrode 41 with the silver layer 57 using a neutral beam sputtering apparatus 60 shown in FIG. 19. More specifically, a sensor base 65 is mounted on a sample support 66, and a silver chloride target and a polytetrafluoroethylene resin target 63 set on a target support 67 were bombarded alternately and repeatedly with a switching interval of 30 minutes and for a total period of 6 hours by a high-speed argon atom beam (0.5 Standard Cubic Centimeter per Minute (SCCM) in argon gas flow rate, 1.15 to 1.2 mA in current) 62 produced from a high-speed atom beam gun 61 by ionizing argon gas at 7 kV, accelerating the ions and then neutralizing them again by producing an electron shower to cause deposition of flyingout particles 64 on the surface of the reference electrode section 41 of the sensor base 65, thus forming a lamination film 58 with a thickness of 300 to 500 angstroms. The silver chloride layers and polytetrafluoroethylene layers in the lamination film 58 each had a thickness of 30 to 50 angstroms. In FIG. 19, designated at 61a is a high voltage power source for the high-speed atom beam gun, 66a and 67a drive motors for rotating the sample support 66 and target support 67, respectively, and 69 an exhausting pump.

Experiment Example 11

Figure 20:
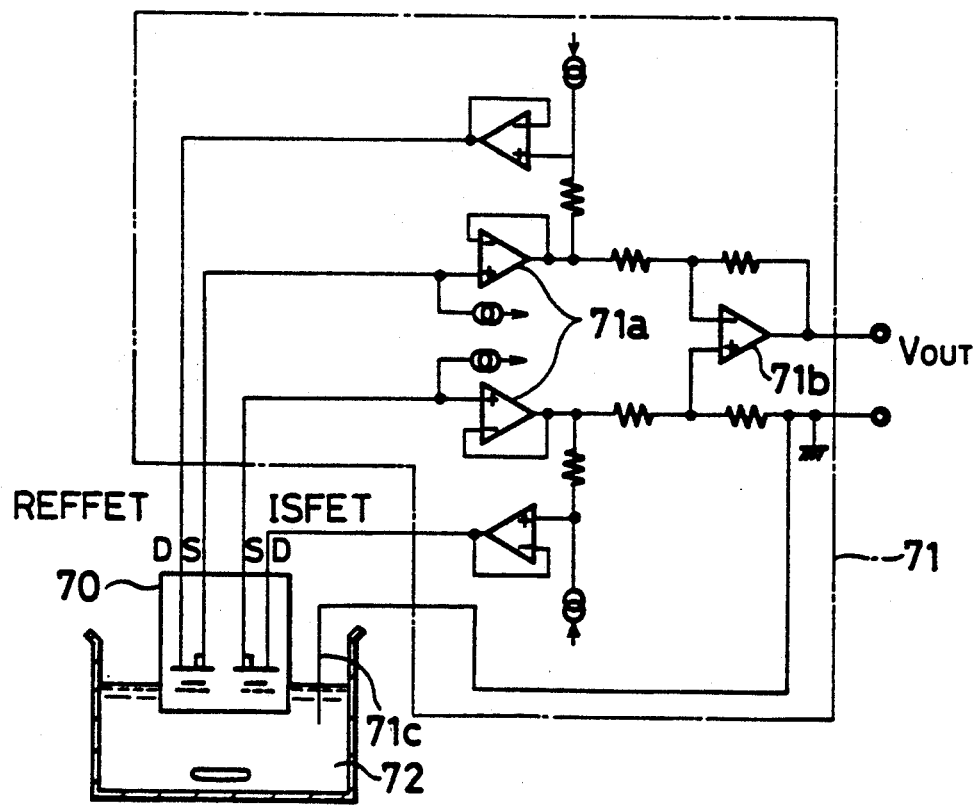
FIG. 20 is a circuit diagram showing a measuring unit used in Experiment example 12.
Figure 21:
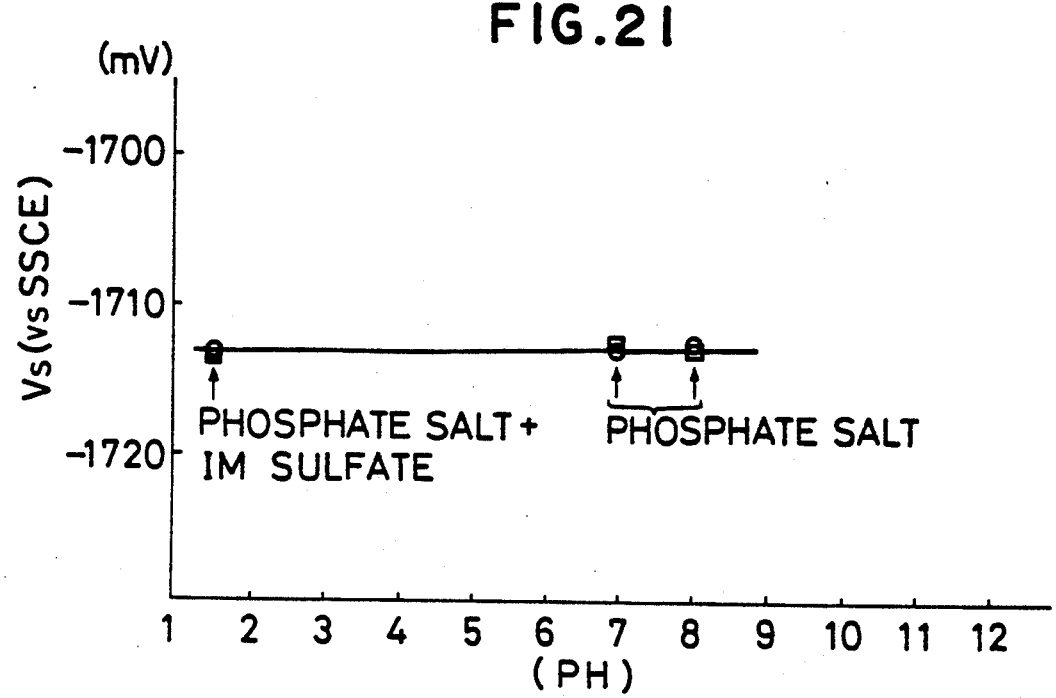
FIG. 21 is a graph showing a response characteristic of an ISFET sensor produced in Experiment example 15.

The ISFET ion sensor 70 produced in Embodiment 15 was connected to a measuring unit 71 shown in FIG. 20 and then held immersed in an aqueous solution 72 of an electrolytic salt to examine its response characteristic. In the measuring unit 71, the source-drain voltage $V_{DS}$ of the reference electrode section 41 and sensor section 42 was set to 4 V for constant current driving with a source current of 50 $\mu$A, and the source potential difference Vout between the reference electrode section 41 and sensor section 42 was provided from the output terminal of a comparator 71b. A common electrode 71c was also held immersed in the solution to provide for electric neutrality of the circuit. FIG. 21 shows the result of measurement. In the Figure, the circle mark represents a result with a water solution not containing NaCl, and a square mark that of a solution containing 0.2 M of NaCl. In the respective experiment examples as shown in FIG. 21, phosphate salt and phosphate salt with IM sulfate have been used.

It was found that while the output potential was extraordinarily low, a constant potential ($-1713$ mV) was provided irrespective of the Cl$^-$ ion concentration or pH of the solution. The ion sensor thus was found to have characteristics necessary for the reference electrode.

(Embodiment 16)

An ISFET ion sensor having a MOSFET structure as shown in FIG. 18 was produced. More specifically, a p-type well region 82 and then source and drain regions 83 and 84 were formed through impurity diffusion in areas of a n-type silicon substrate 81, in which reference electrode section 41 and sensor section 42 were to be formed, after the process of manufacture of a n-channel MOSFET. Subsequently, a silicon oxide film 85 with a thickness of 1,000 angstroms and a silicon nitride film with a thickness of 1,500 angstroms were formed to cover the entire surface. Subsequently, a silver layer 57 and then a lamination film 58 were formed on the reference electrode section 41 in the manner as in Embodiment 15.

Experiment Example 12

Figure 22:
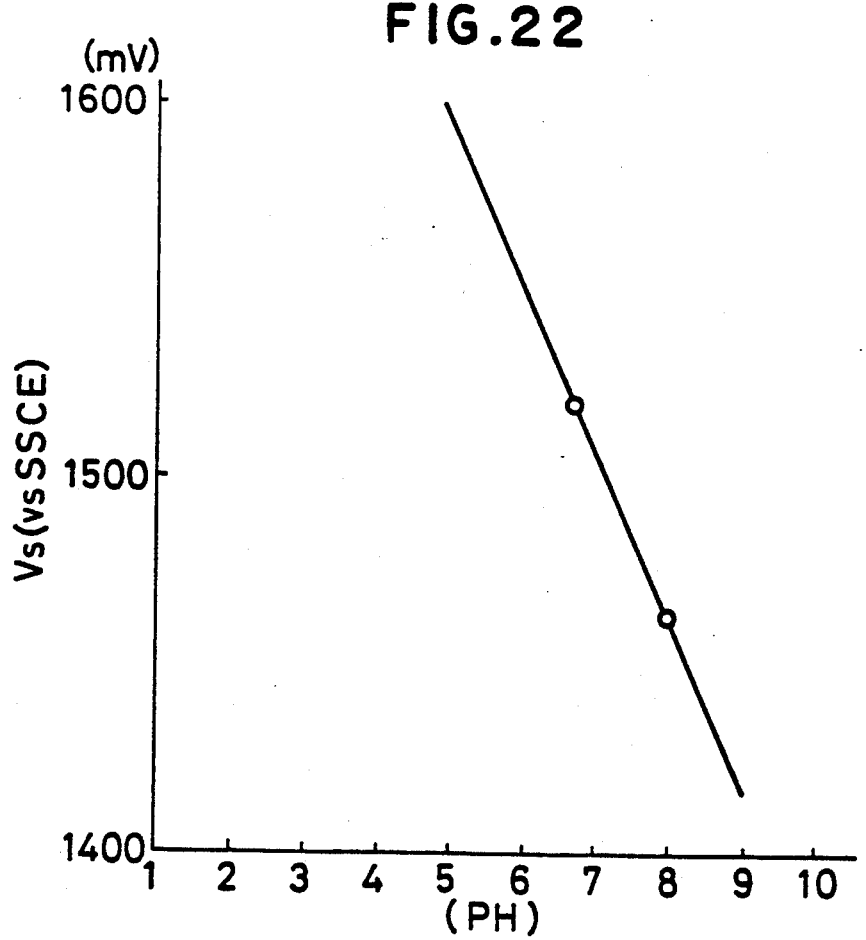
FIG. 22 is a graph showing a response characteristic of an ISFET sensor produced in Embodiment 16.

The response characteristic of the ISFET ion sensor 6.8 and 8.0 was measured using a reference ISFET for reference. FIG. 22 shows the result. The obtained response characteristic had a slope of about $-45.9$ mV/pH.

While in the above embodiment a pH sensor was used as ion sensor to be combined with the reference electrode, the sensor can of course be combined with all other ion sensors, enzyme sensors, bio-sensors, gas sensors and the like, the output potential of which is measured for detection.

(Embodiment 17)

Figure 23:
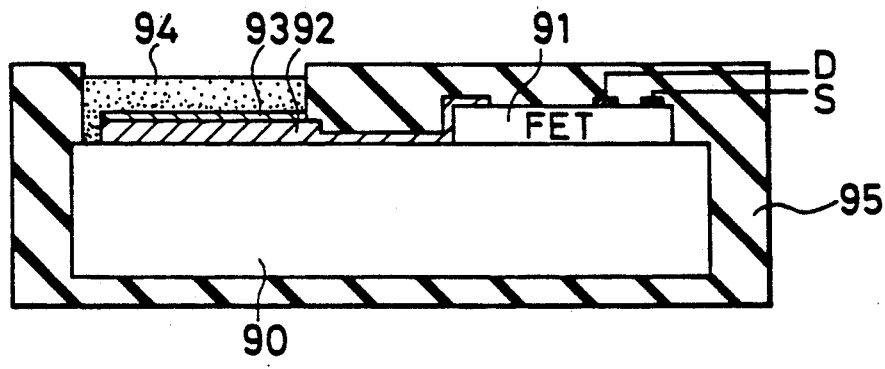
FIG. 23 is a sectional view showing an ion sensor as Embodiment 17.

A MOSFET 91 was formed on a surface of a SOS substrate 90, as shown in FIG. 23, by utilizing an ordinary process of semiconductor manufacture, and then a graphite layer 92 with a thickness of 1,000 angstroms was formed FET 91. At this time, a metal mask (i.e., molybdenum mask) with a thickness of 20 microns was used for the patterning of the gate electrode.

Subsequently, a redox function film 92 with a thickness of about 1,000 angstroms was formed on the graphite layer 92 by the following method.

Figure 25:
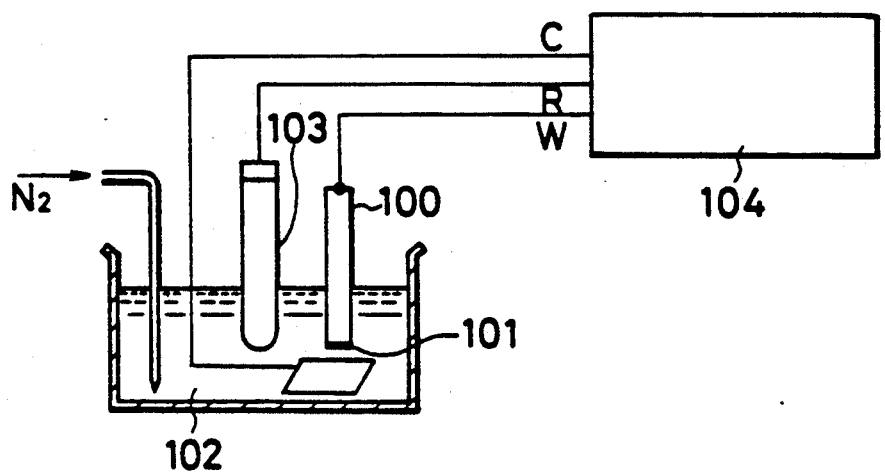
FIG. 25 is a schematic view showing an electrolytic unit used in Experiment examples 13 to 17.

First, as shown in FIG. 25, an isotropic graphite rod 100 with a diameter of 15 mm and a length of 5 mm was electrolytically decomposed under the following conditions to form a poly-(4,4'-biphenol) film 101 with a thickness of 150 microns as target on a substrate surface. As the electrolyte was used a blend liquid (at a temperature of 20° C.) composed of 0.01 M of 4,4'-biphenol, 0.5 M of NaClO$_4$ and acetonitride. The graphite substrate 100 was held immersed in this electrolyte, then the saturated calomel electrode (SCE) 103 was swept from 0 to 1.5 V (at a sweeping rate of 50 mV/sec.) three times, and then a constant potential electrolytic reaction was caused to proceed at 1.5 V for 20 minutes using an electrolysis unit 104.

The graphite substrate 100 clad with an electrolytically polymerized film thus obtained was then taken out and secured with the electrolytically polymerized film up to the target support 67 of the neutral beam sputtering apparatus 60 shown in FIG. 19. To the sample support 66 was secured a MOSFET with a graphite film formed on a gate section. At this time, a metal mask of about 50 microns was mounted to let the entire surface of graphite on the gate section be covered by the spattered film. Then, the surface of the target (i.e., electrolytically decomposed film here) was caused to be bombarded by an argon atom beam (with an initial speed of $3 \times 10^6$ cm/sec. or above) produced by operating the highspeed atom beam gun 21 of the sputtering apparatus 60 under a reduced pressure of $10^{-4}$ to $10^{-5}$ Torr, and sputtered particles were caused to be deposited on the surface of the MOSFET for 6 hours, thus forming a redox function film 93 with a thickness of 1,000 angstroms. Subsequently, the gate film was annealed overnight in vacuum and at room temperature, and then was preserved in nitrogen gas.

On the surface of the MOSFET gate film thus produced, an ion-sensitive film formation solution having a compositions shown in Table 1 was dropped several times each by about 10 microlitres using a microdispenser, and then the solvent was dried away, thus forming an ion-sensitive film (or ion selectivity film) 94 having a thickness of 10 to 20 microns.

After the gate film was formed in this way, it was electrically insulated with an insulating adhesive film 95.

TABLE 1

| Experiment example | Detected ions | Ion carrier composition | | | |
|---|---|---|---|---|---|
| | | Carrier substance (content: mg/ml) | KTpClPB (mg/ml) | PVC (mg/ml) | DOS (mg/ml) |
| 13 | K$^+$ | Barinomicine 3.2 | | 65.6 | 131.2 |
| 14 | Na$^+$ | Bis-12-Crown-4 5.0 | 1.1 | 65.0 | 129 |
| 15 | Cl$^-$ | TPSnCl 11.2 | | 63.0 | 125.8 |
| 16 | Ca$^{2+}$ | Ca(DOPO)$_2$ | | | |

TABLE 1-continued

| Experiment example | Detected ions | Carrier substance (content: mg/ml) | KTpClPB (mg/ml) | PVC (mg/ml) | DOS (mg/ml) |
|---|---|---|---|---|---|
| | | 14.0 DOPO 62.0 | | 62.0 | 62.0 |
| 17 | $Mg^{2+}$ | DHMBA 6.25 | 1.25 | 80.5 | 160 |

*THE(tetrahydrofuran) was used as solvent in all the examples.
The abbreviations of ion carrier substance represent the following.
Bis-12-Crown-4: Bis-(12-crown-4)-methyl-dodecylmaronate (manufactured by Dojinkagakusha)
TPSnCl: Triphenyl tin chloride (manufactured by Aldrich Inc.)
Ca(DOPO): Calcium bis-di-(n-octylphenyl)-phosphate (manufactured by Dojinkagakusha)
DOPO: Di-(n-octylphenyl)-phosphate (manufactured by Dojinkagakusha)
DHMBA: N,N'-diheptyl-N,N'-dimethyl-1,4-butadiamide (manufactured by Fluka Co., Ltd.)

In the carrier composition, KTpClPB represents potassium tetrakis-(p-chlorophenyl)-borate, PVC represents polyvinyl chloride, and DOS represents sebacic acid dioctyl.

Experiment examples 13 to 17

Figure 26:
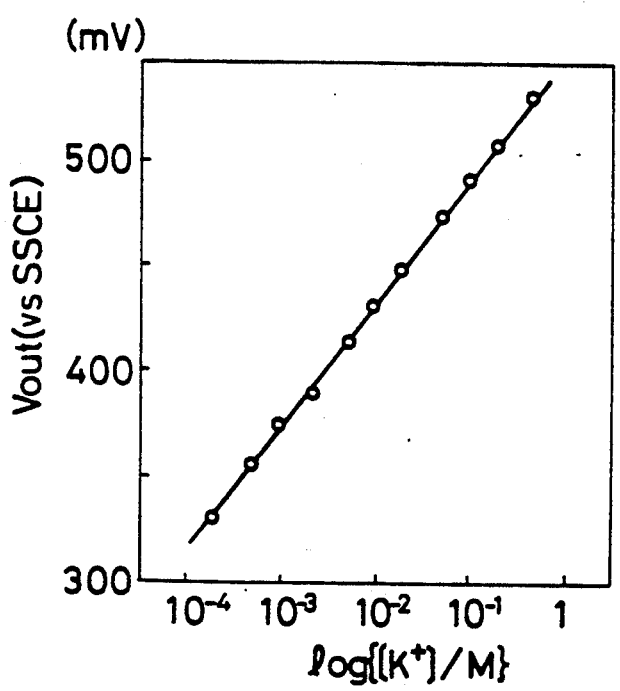
FIG. 26 is a graph showing the result of test conducted in Experiment example 13 on a potassium ion sensor produced in Embodiment 17.

The FET potassium ion sensor 70 produced in Embodiment 17 was connected to the measuring unit shown in FIG. 6 and held immersed together with saturated sodium chloride saturated calomel electrode (SSCE) 21 as reference electrode in a cell, and the output voltage was measured by varying the potassium ion concentration in the solution. The output voltage Vout was in a good linear relation to the logarithmic values of potassium ion concentration, as shown in FIG. 26. The slope of the plot was 60.5 mV/log{[K+]/M } (37° C.), and the linearity range was $10^{-4}$ to $5\times10^{-1}M$. The response time was found to be as quick as 95% in one second. Further, it was found that the output voltage was difficult to influence by illumination intensity changes and oxygen partial pressure. As FET drive conditions, the drain-source voltage $V_{DS}$ was set to 4 V, and the source current $I_s$ to 50 $\mu A$. While the results obtained with Experiment examples 14 to 17 are not shown, they were sufficient as characteristics of ion sensor.

(Embodiment 18)

Figure 24:
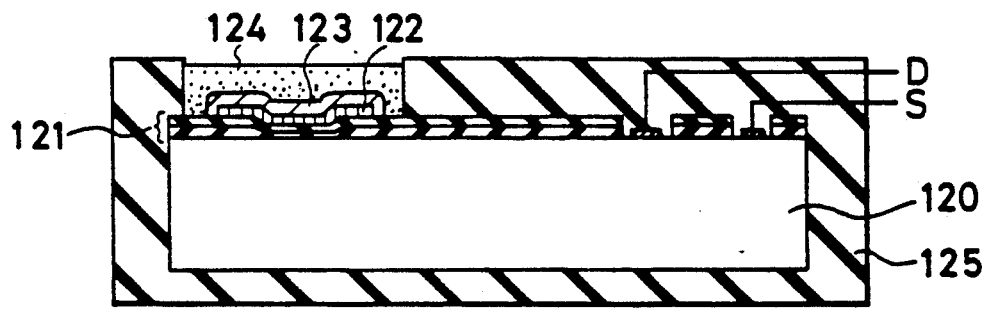
FIG. 24 is a sectional view showing an ion sensor as Embodiment 18.

As shown in FIG. 24, a source-drain section was formed on a p-type silicon substrate (10 to 20 $\Omega$.cm) 120 by utilizing ordinary semiconductor manufacture process techniques, and then a gate insulation film 121 consisting of a silicon oxide (SiO) film with a thickness of about 1,000 angstroms and a silicon nitride ($Si_3N_4$) film with a thickness of 1,500 angstroms was formed on the gate section. Further, a graphite layer with a thickness of about 1,000 angstroms was formed on the gate section at 1,100° to 1,200° C. using the CVD process. Then a resist was spin-coated and patterned. Subsequently, the exposed graphite layer was etched in hydrogen plasma, and then the resist was removed to leave a graphite layer 122 on the sole gate section. Then, like Embodiment 17 a poly-(4,4'-biphenol) film with a thickness of about 1,000 angstroms was formed as redox function film 123 using a neutral atom beam sputtering apparatus, and then an ion-sensitive film 124 having a composition as shown in Table 1 and with a thickness of about 10 microns was formed. After a gate film was thus formed, it is electrically insulated with an insulating adhesive layer 125.

(Embodiment 19)

A silver layer was deposited by a vacuum deposition process on a gate section of a reference electrode section of a twin ISFET produced in a manner like that in Embodiment 15, and then a silver chloride layer with a thickness of about 100 angstroms was formed using a vacuum deposition apparatus (of EB heating type). Then, a polytetrafluoroethylene (PTFE) thin film with a thickness of 20 to 50 angstroms was formed under conditions like those in Embodiment 15 using the neutral beam sputtering apparatus 60 noted above, and then a silver chloride layer with a thickness of 20 to 50 angstroms was formed using the vacuum deposition apparatus noted above. The above operations of film formation were repeatedly performed 5 to 10 times to form a polytetrafluoroethylenesilver chloride lamination film with a thickness of 400 to 800 angstroms.

Experiment examples 18 to 22

Response characteristic examination was carried out in the same manner as in Experiment examples 13 to 17 except for that an ISFET sensor shown in FIG. 24 was used in lieu of the ISFET sensor shown in FIG. 23. The results obtained were similar to those in Experiment examples 13 to 17.

Experiment example 23

An ISFET sensor produced in Embodiment 19 was examined with the measuring apparatus shown in FIG. 20. Similar results to those in Experiment example 11 could be obtained.

What is claimed is:

1. An ion sensor comprising an electrically conductive substrate, and redox function film formed by a neutral atom beam sputtering process on a surface of said substrate and an ion-sensitive film covering said redox function film.

2. An ion sensor comprising a gate insulation film of a MOS field-effect transistor, and a redox function film formed by a neutral atom beam sputtering process on a surface of said gate insulation film and an ion-sensitive film covering said redox function film.

3. A method of manufacturing an ion sensor comprising a step of forming a target of a redox function substance on a predetermined substrate surface, a step of sputtering said target by projecting a neutral atom beam onto said redox function substance to thereby form a redox function film on said substrate surface and a step of forming an ion-sensitive film on a surface of said redox function film.

4. An ion sensor comprising:
   an electrically conductive first substrate;
   a redox function film formed on a surface of said first substrate by preparing a film formed on a second electrically conductive substrate by an electrolytic polymerization process, and then sputtering the electrolytically polymerized film as a target by a neutral atom beam, thereby depositing sputtered particles on the surface of said first substrate; and
   an ion-sensitive film covering said redox function film.

5. An ion sensor comprising:
   a gate insulation film of a MOS filed effect transistor;
   a redox function film formed on a surface of said gate insulation film by preparing a film formed on a predetermined substrate by an electrolytic polymerization process, and then sputtering the electrolytically polymerized film as a target by a neutral atom beam, thereby depositing sputtered particles on the surface of said gate insulation film; and
   an ion-sensitive film covering said redox function film.

* * * * *

UNITED STATES PATENT AND TRADEMARK OFFICE
CERTIFICATE OF CORRECTION

PATENT NO. : 5,213,675
DATED : May 25, 1993
INVENTOR(S) : Shuichiro Yamaguchi, et. al.

It is certified that error appears in the above-indentified patent and that said Letters Patent is hereby corrected as shown below:

Column 1, line 36, delete "are" and insert -- is --.
Column 1, line 63, delete "films is" and insert --film are --.
Column 2, line 8, delete "difficultly" and insert --difficult--.
Column 3, line 15, delete "polyhydroxymethyl-methacrylate" and insert-- polyhydroxyethyl-methacrylate --.
Column 4, line 50, delete "there" and insert -- thereon --.
Column 14, line 18, delete "acetonitride" and insert -- acetonitrile --.

Signed and Sealed this

Twenty-second Day of February, 1994

Attest:

BRUCE LEHMAN

*Attesting Officer*  *Commissioner of Patents and Trademarks*